US007232565B2

(12) United States Patent
Henson et al.

(10) Patent No.: US 7,232,565 B2
(45) Date of Patent: Jun. 19, 2007

(54) USE OF ENDOPHYTIC FUNGI TO TREAT PLANTS

(75) Inventors: Joan M. Henson, Bozeman, MT (US); Kathy B. Sheehan, Bozeman, MT (US); Russell J. Rodriguez, Seattle, WA (US); Regina S. Redman, Seattle, WA (US)

(73) Assignee: Montana State University, Bozeman, MT (US)

( * ) Notice: Subject to any disclaimer, the term of this patent is extended or adjusted under 35 U.S.C. 154(b) by 380 days.

(21) Appl. No.: 10/602,546

(22) Filed: Jun. 23, 2003

(65) Prior Publication Data

US 2004/0082474 A1    Apr. 29, 2004

Related U.S. Application Data

(60) Provisional application No. 60/390,515, filed on Jun. 21, 2002.

(51) Int. Cl.
    *A01N 63/04*    (2006.01)
(52) U.S. Cl. .................... 424/93.5; 504/117; 435/254.1
(58) Field of Classification Search ...................... None
    See application file for complete search history.

(56) References Cited

U.S. PATENT DOCUMENTS 5,880,343 A    3/1999    Hiruma et al.

OTHER PUBLICATIONS

DE Luna, L.Z., Watson, A.K., Paulitz, T.C. Reaction of Rice (*Oryza sativa*) Cultivars to Penetration and Infection by *Curvularia tuberculata* and *C. oryzae*. Plant Disease. 86: 470-476. 2002.*
Azevedo et al., "Endophytic, microorganisms: a review on insect control and recent advances of tropical plants", EJB Electronic J. of Biotechnology, Apr. 2000, 3(1):40-65.
Bacon, C.W., "Abiotic stress tolerances (moisture, nutrients) and photosynthesis in endophyte-infected tall fescue", Agricult. Ecosys. Environ., 1993, 44:123-141.
Bacon, C.W., et al., "Microbial Endophytes", 2000, Marcel Dekker Inc., N.Y.
Bordallo, J.J., et al., "Colonization of plant roots by egg-parasitic and nematode-trapping fungi", New Phytol., 2002, 154:491-499.
Caretta et al., "Some filamentous fungi on grassland vegetation from Kenya", Mycophatholgia, 1999, 145:155-169.
Carroll, G.C., "The biology of endophytism in plats with particular reference to woody perennials", Microbiology of the Phyllosphere (eds. Fokkema, H.J. & Van Den Heuvel, J.) 205-222 (Cambridge University Press, Cambridge, 1986).
Clay, K., et al., "Fungal endophyte symbiosis and plant diversity in successional fields", Science, 1999, 285:1742-1744.
De Bary, A., "Die Erschenung Symbiose", in Vortrag auf der Versammlung der Naturforscher und Artze zu Cassel, ed. Trubner, K.J., 1-30, Strassburg, 1879.

Freeman, S., et al., "Genetic conversion of a fungal plant pathogen to a nonpathogenic, endophytic mutualist", Science, 1993, 260:75-78.
Ghosh et al., "Soil fungi from Orissa (India)-I", Mycologia, 1960, 52:915-918.
Hertig, M., et al., "The terms symbiosis, symbiont and symbiote", J. Parasit., 1937, 23:326-329.
Hodges et al., "Growth of Agrostis palustris in response to adventitious root infection by *Curvularia lunata*", J. Phytopathol., 1995, 143:639-642.
Jain, B.L., "Two new species of *Curvularia*", Trans. Br. Mycol. Soc., 1962, 45:539-544.
Jumpponen, A., et al., "Dark septate endophytes: a review of facultative biotrophic root-colonizing fungi", New Phytol., 1998, 140:295-310.
Kuldau, G.A., et al., in *Microbial Endophytes* C. W. Bacon, J. F. White Jr., Eds. (Marcel Dekker, Inc., New York, 2000) pp. 85-117.
Latch, G.C.M., Physiological interactions of endophytic fungi and heir hosts, Biotic stress tolerance imparted to grasses by endophytes, Agricult. Ecosys. Environ., 1993, 44:143-156.
Lewis, D.H., "Symbiosis and mutualism: crisp concepts and soggy semantics", The biology of Mutualism (ed. Boucher, D.H.) 29-39, Croom Helm Ltd., London, 1985.
Marks, S., et al., "Effects of CO2 enrichment, nutrient addition, and fungal endophyte-infection on the growth of two grasses", Oecologia, 1990, 84:207-214.
Morton, J.B., "Biodiversity and evolution in mycorrhizae in the desert", Microbial Endophytes (eds. Bacon, C.W. & White, J.F.J.) 3-30 (Marcel Dekker, Inc., New York, NY, 2000).
Petrini, O., "Taxonomy of endophytic fungi of aerial plant tissues", 1986, Microbiology of Phyllosphere (eds. Fokkema, N.J. & van den Heuvel, J., 175-187, Cambridge University Press, Cambridge.
Pirozynski et al, "The origin of land plants: a matter of mycotrophism", Biosystems, 1975, 6:153-164.
Read, D.J., "Mycorrhiza-the state of the art", Mycorrhiza (eds. Varma, A. & Hock, B.) 3-34 (Springer-Verlag, Berlin, 1999).
Redecker et al., "Fungi from the Ordovician", Science, 2000, 289:1920-1921.
Redman et al., "Biochemical analysis of plant protection afforded by a nonpathogenic endophytic mutant of *Collectotrichum magna*", Plant Physiol., 1999, 119:795-804.
Redman et al., Fungal symbiosis: from mutualism to parasitism, who control the outcome, host or invader? New Phytol., 2001, 151:705-716.

(Continued)

*Primary Examiner*—Irene Marx
(74) *Attorney, Agent, or Firm*—Cooley Godward Kronish LLP

(57) ABSTRACT

The present invention is directed to methods and compositions of endophytic fungi that confer stress tolerance in inoculated plants, including both monocots and dicots. In particular, *Curvularia* species, isolated from a host grass *Dichanthelium languinosum* growing in the geothermal zones of Lassen Volcanic and Yellowstone National Parks, confers such stress tolerance. Upon inoculating a target plant or plant part with endophytic fungi, the resulting plant shows stress tolerance, particularly drought and thermal tolerance.

8 Claims, 5 Drawing Sheets

OTHER PUBLICATIONS

Figure 1:
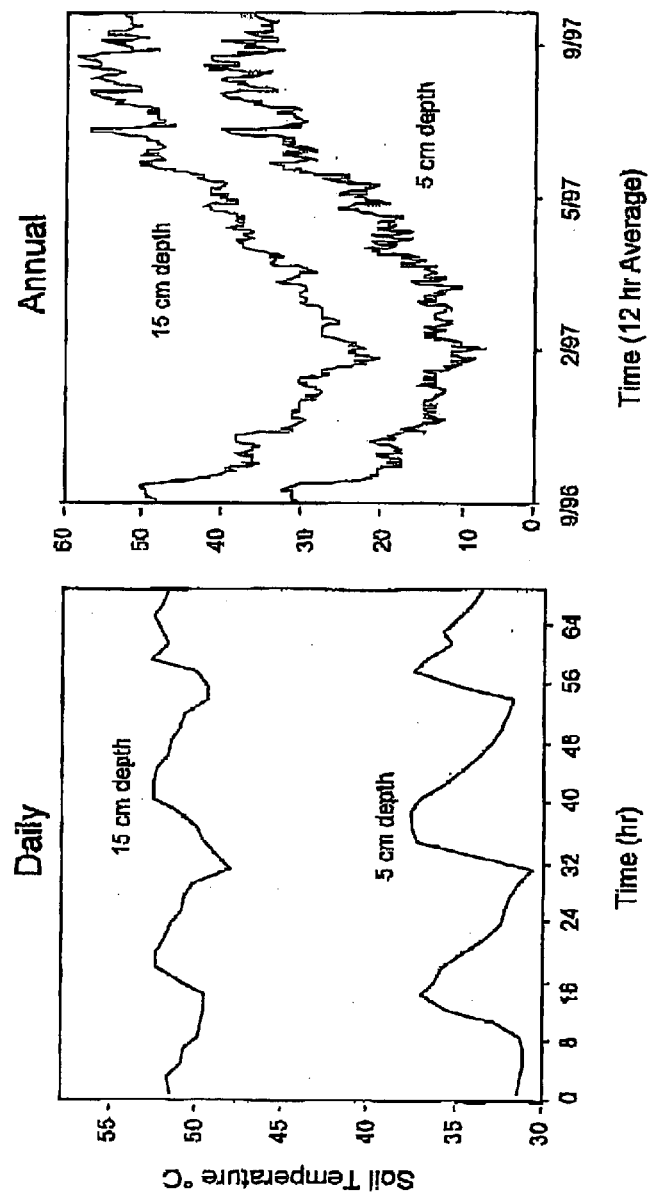

Redman et al., "Thermotolerance Generated by Plant/Fungal Sympbiosis", *Science*, vol. 298, Nov. 22, 2002, 1581.

Redman, R.S., et al., Field performance of cucrbit and tomato plants colonized with a nonpathogenic mutant of *Colletotrichum magna* (telemorph: *Glomerella magna*; Jenkins and Winstead), 2002, Symbiosis, 32:55-70.

Saikkonen, K., et al., *Annu. Rev. Ecol. Syst.* 29, 319-343 (1998).

Schultz, B., "Bioactive Fungal Metabolites-Impact Exploitation", 2001, British Mycological Society, International Symposium Proceedings, University of Wales, April.

Simon et al., "Origin and diversification of endomycorrhizal fungi and coincidence with vascular land plants", Nature, 1993, 363:67-69.

Smallwood, M.F., et al., "Plant Responses to Environmental Stress", 1999, BIOS Scientific Publishers Limited, Oxford.

Smith, A.F., et al., "Structural diversity in (vesicular)-arbuscular mycorrhizal symbioses", New Phytol., 1997, 137:373-388.

Smith, K.P, et al., "Host variation for interactions with beneficial plant-associated microbes", Annu. Rev. Phytopathol., 1999, 37:473-492.

Stone, J.K., et al., in *Microbial Endophytes* C. W. Bacon, J. F. White Jr., Eds. (Marcel Dekker, Inc., New York, 2000) pp. 3-29.

Taylor et al., "Endophytic fungi associated with the temperate palm *Trachycarpus fortunei*, within and outside its natural geographic range", New Phytologist, May 1999, 142(2):335-346.

Varma, A., et al., "*Pirifmospora indica*, a cultivable plant-growth-promoting rood endophyte", App. Environ. Microbiol., 1999, 65:2741-2744.

\* cited by examiner

Non-symbiotic

Symbiotic with *C. magna* path-1

Symbiotic with *Curvularia sp.* 1A15.1

USE OF ENDOPHYTIC FUNGI TO TREAT PLANTS

This application claims the benefit of U.S. Provisional Application No. 60/390,515, filed Jun. 21, 2002.

FIELD OF THE INVENTION

The invention relates to the use of endophytic fungi, particularly *Curvularia* species, to treat plants, including both monocots and dicots. The treatment results in the host plant acquiring stress tolerance, in particular to either drought or thermal tolerance.

BACKGROUND OF THE INVENTION

In the past few decades, plant scientists have begun to realize that plants may be serving as a reservoir of untold numbers of organisms known as endophytes (Bacon, C. W., and White, J. F. 2000. Microbial Endophytes. Marcel Deker Inc., N.Y.). By definition, these microorganisms (mostly fungi and bacteria) live in the intercellular spaces of plant tissues. Some of these endophytes may be producing bioactive substances that, in some way, may be involved in the host endophyte relationship. As a direct result of the role that these secondary metabolites may play in nature, they may ultimately be shown to have applicability in medicine, agriculture and industry. We are now witnessing the beginning a worldwide scientific effort to isolate endophytes and study their natural products. While there are myriads of epiphytic microorganisms associated with plants, the endophytic ones seem to be attracting more attention. This may be the case since closer biological associations may have developed between these organisms in their respective hosts than the epiphytes. Hence, the result of this may be the production of a greater number and diversity of classes of biological derived molecules possessing a range of biological activities. In fact, a recent comprehensive study has indicated that 51% of biologically active substances isolated from endophytic fungi were previously unknown (Schutz, B. 2001. British Mycological Society, International Symposium Proceedings, Bioactive Fungal Metabolites—Impact and Exploitation. University of Wales, April.). This compares with only 38% novel substances from soil microflora.

One of the least studied biochemical-chemical systems in nature is the relationship existing between microorganisms and their plant hosts. For instance, it does appear that all higher plants are hosts to one or more endophytic microbes. These microbes include the fungi, bacteria and actinomycetes and reside in the tissues beneath the epidermal cell layers. It is well understood that endophytic infections are at least inconspicuous. And as a result, the host tissues are transiently symptomless and the colonization of the tissues is internal to the surface of the plant. The exact physical relationship of the endophyte to the plant has, in most cases, remained obscure because it is extremely difficult, by electron microscopic techniques, to find an endophyte within plant tissues. Conceivably, the microbes live within the intercellular spaces of the tissues and it also seems likely that penetration of living cells may occur but is not easy to observe.

Fossil records indicate that fungi have been associated with plants since at least 400 million years ago (Simon, et al., Origin and diversification of endomycorrhizal fungi and coincidence with vascular land plants, Nature 363, 67–69 (1993); Remy, et al., Four hundred-million-year-old vesicular arbuscular mycorrhizae, Proc. Nat. Acad. Sci. 91, 11841–11843 (1994); Redecker, et al., Fungi from the Ordovician, Science 289, 1920–1921 (2000), all of which are expressly incorporated by reference) and it is theorized that early symbiotic interactions were responsible for the establishment of land plants (Pirozynski, et al., The origin of land plants: a matter of mycotrophism, Biosystems 6, 153–164 (1975), expressly incorporated by reference). Since the first description of plant/fungal symbiosis (De Bary, A., Die Erschenung Symbiose, in Vortrag auf der Versammlung der Naturforscher und Artze zu Cassel (ed. Trubner, K. J.) 1–30 (Strassburg, 1879); Hertig, M., et al., The terms symbiosis, symbiont and symbiote, J. Parasit. 23, 326–329 (1937) all of which are expressly incorporated by reference), all plants studied in natural ecosystems have been found to be symbiotic with fungi (Petrini, O., Taxonomy of endophytic fungi of aerial plant tissues, in Microbiology of the Phyllosphere (eds. Fokkema, N.J. & van den Heuvel, J.) 175–187 (Cambridge University Press, Cambridge, 1986) expressly incorporated by reference). These fungi, termed endophytes, express a variety of symbiotic lifestyles including mutualism, commensalism, or parasitism that positively, neutrally, or negatively affect host fitness, respectively (Lewis, D. H., Symbiosis and mutualism: crisp concepts and soggy semantics, in The Biology of Mutualism (ed. Boucher, D. H.) 29–39, (Croom Helm Ltd, London, 1985), expressly incorporated by reference).

The host range, here defined as the ability to colonize a plant, of most symbiotic fungi is poorly defined. With the exception of vesicular arbuscular mycorrhizae, there are few reports of fungal symbionts asymptomatically colonizing both monocots and eudicots (Smith, A. F. & Smith, S. E., Structural diversity in (vesicular)-arbuscular mycorrhizal symbioses, New Phytol. 137, 373–388 (1997); Jumpponen, A. & Trappe, J. M., Dark septate endophytes: a review of facultative biotrophic root-colonizing fungi, New Phytol. 140, 295–310 (1998); Bordallo, J. J. et al., Colonization of plant roots by egg-parasitic and nematode-trapping fungi, New Phytol. 154, 491–499 (2002) all of which are expressly incorporated by reference). This may indicate host range limitations or a limited number of plant taxa analyzed during host range studies. Moreover, individual fungi can express different lifestyles in different plant hosts and, although the basis of symbiotic communication responsible for the outcome of these associations (mutualistic, commensal, or parasitic) is unknown, lifestyle expression appears to be controlled by the plant genome (Smith, K. P. & Goodman, R. M., Host variation for interactions with beneficial plant-associated microbes, Annu. Rev. Phytopathol. 37, 473–492 (1999); Redman, et al., Fungal symbiosis: from mutualism to parasitism, who controls the outcome, host or invader? New Phytol. 151, 705–716 (2001) all of which are expressly incorporated by reference).

Adaptation of plants to selective pressures is also considered to be regulated by the plant genome (Smallwood, M. F., Calvert, C. M. & Bowles, D. J. Plant Responses to Environmental Stress (BIOS Scientific Publishers Limited, Oxford, 1999) expressly incorporated by reference). However, recent studies indicate that fitness benefits conferred by mutualistic fungi contribute to plant adaptation (Clay, K. & Holah, J., Fungal endophyte symbiosis and plant diversity in successional fields, Science 285, 1742–1744 (1999); Morton, J. B., Biodiversity and evolution in mycorrhizae in the desert, in Microbial Endophytes (eds. Bacon, C. W. & White, J. F. J.) 3–30 (Marcel Dekker, Inc., New York, N.Y., 2000); Redman, et al., Thermotolerance conferred to plant host and fungal endophyte during mutualistic symbiosis. Science In Press (2003) all of which are expressly incorporated by reference). Mutualistic fungi may confer tolerance to drought (Bacon, C. W., Abiotic stress tolerances (moisture, nutrients) and photosynthesis in endophyte-infected tall fescue, Agricult. Ecosys. Environ. 44, 123–141 (1993); Read, D. J., Mycorrhiza—the state of the art, in Mycorrhiza (eds. Varma, A. & Hock, B.) 3–34 (Springer-Verlag, Berlin, 1999) all of which are expressly incorporated by reference), metals (Read, D. J., Mycorrhiza—the state of the art, in Mycorrhiza (eds. Varma, A. & Hock, B.) 3–34 (Springer-Verlag, Berlin, 1999) all of which are expressly incorporated by reference), disease (Carroll, G. C., The biology of endophytism in plants with particular reference to woody perennials, in Microbiology of the Phyllosphere (eds. Fokkema, N. J. & Van Den Heuvel, J.) 205–222 (Cambridge University Press, Cambridge, 1986); Freeman, S. & Rodriguez, R. J., Genetic conversion of a fungal plant pathogen to a nonpathogenic, endophytic mutualist. Science 260, 75–78 (1993); Redman, et al. Biochemical analysis of plant protection afforded by a nonpathogenic endophytic mutant of *Colletotrichum* magna. Plant Physiol. 119, 795–804 (1999) all of which are expressly incorporated by reference), and herbivory (Latch, G. C. M. Physiological interactions of endophytic fungi and their hosts, Biotic stress tolerance imparted to grasses by endophytes, Agricult. Ecosys. Environ. 44, 143–156 (1993) expressly incorporated by reference), and/or promote growth (Marks, S. & Clay, K., Effects of CO2 enrichment, nutrient addition, and fungal endophyte-infection on the growth of two grasses, Oecologia 84, 207–214 (1990); Varma, A. et al., Pirifmospora indica, a cultivable plant-growth-promoting root endophyte, App. Environ. Microbiol. 65, 2741–2744 (1999); Redman, R. S. et al., Field performance of cucurbit and tomato plants colonized with a nonpathogenic mutant of *Colletotrichum magna* (teleomorph: *Glomerella magna*; Jenkins and Winstead), Symbiosis 32, 55–70 (2002) all of which are expressly incorporated by reference) and nutrient acquisition (Read, D. J., Mycorrhiza—the state of the art, in Mycorrhiza (eds. Varma, A. & Hock, B.) 3–34 (Springer-Verlag, Berlin, 1999) expressly incorporated by reference).

However, microbes have not been cultured from plants in geothermal soils or reported to contribute to the survival of these plants.

Accordingly, there is a need for compositions and methods to treat plants, including both monocots and dicots, to confer stress tolerance, particularly thermal and drought tolerance.

SUMMARY OF THE INVENTION

In accordance with the objects outlined herein, the present invention provides methods of treating a target plant to confer stress tolerance comprising inoculating the plant or a part of the plant with a culture of *Curvularia*. The stress tolerance conferred to the plant may be, for example, thermal tolerance or drought tolerance. Target plants of the invention include, for example, monocots, including grasses or wheats, and dicots, including eudicots. Plant parts of the invention include, for example, seeds and seedlings.

In a further aspect, the present invention provides methods of treating a target plant to confer growth enhancement comprising inoculating the plant or a part of the plant with a culture of *Curvularia*.

In yet a further aspect, the present invention provides a composition comprising a pure culture of *Curvularia*.

DETAILED DESCRIPTION OF THE DRAWINGS

FIGS. 1A and 1B depict the soil temperatures monitored at 5 and 15 cm depths at Amphitheater Springs, Yellowstone National Park. The daily temperatures were collected in June, 1997 (FIG. 1A) and the annual temperatures from September, 1996–September, 1997 (FIG. 1B).

Figure 2:
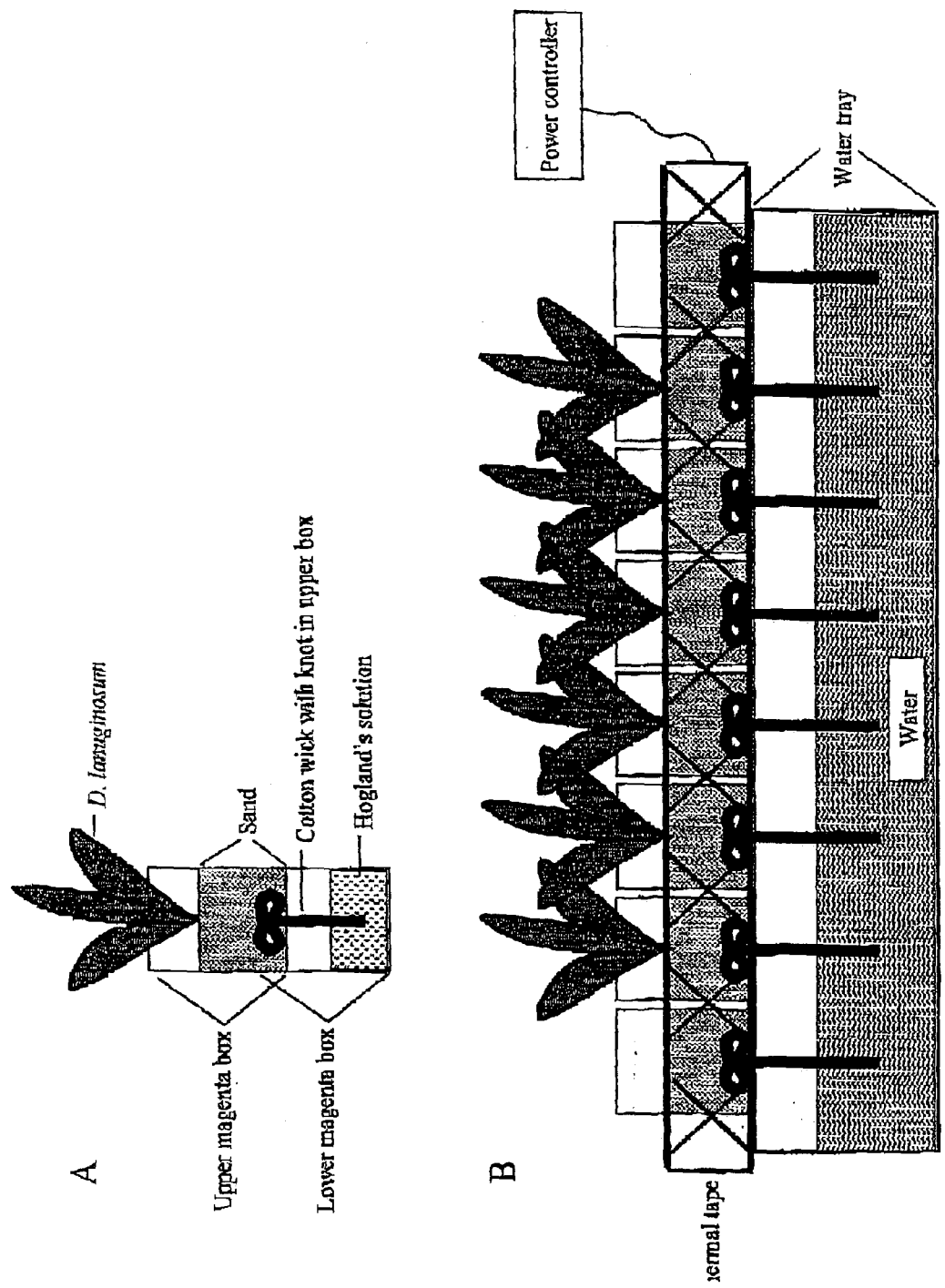

FIGS. 2A and 2B Thermal soil simulator. FIG. 2A) Plants were grown in magenta boxes (Sigma, St. Louis). Prior to planting seeds, a ¼" hole was drilled into the bottom of the magenta box and a cotton wick with a knot at one end was inserted into the hole to extend 4" below the box. Boxes were filled with 2" of sand and placed into a second magenta box containing Hoagland™s solution and sterilized (D. R. Hoagland, D. I. Arnon, *Circular* 347 (University of California, 1938) expressly incorporated by reference). B) Six magenta boxes containing five symbiotic or non-symbiotic *D. lanuginosum* seedlings were placed in a row and the lower boxes removed. The end boxes insulated the adjacent boxes such that sand temperatures were equivalent in all six boxes containing plants. Two-inch wide thermal tape (Cole-Parmer) was supported with 24"×2" metal bars and C-clamped to the outside of the magenta boxes at the sand level. Clamped boxes were set on top of a 20"×7" plastic tray containing ambient temperature, sterile water. Cotton wicks from the magenta box extended below the water line to maintain soil moisture throughout the experiment. The thermal tape was plugged into a power controller to regulate soil temperature. Thermometers were placed 5 cm deep into the soil of each magenta box to ensure that plants were exposed to the same temperatures.

Figure 3:
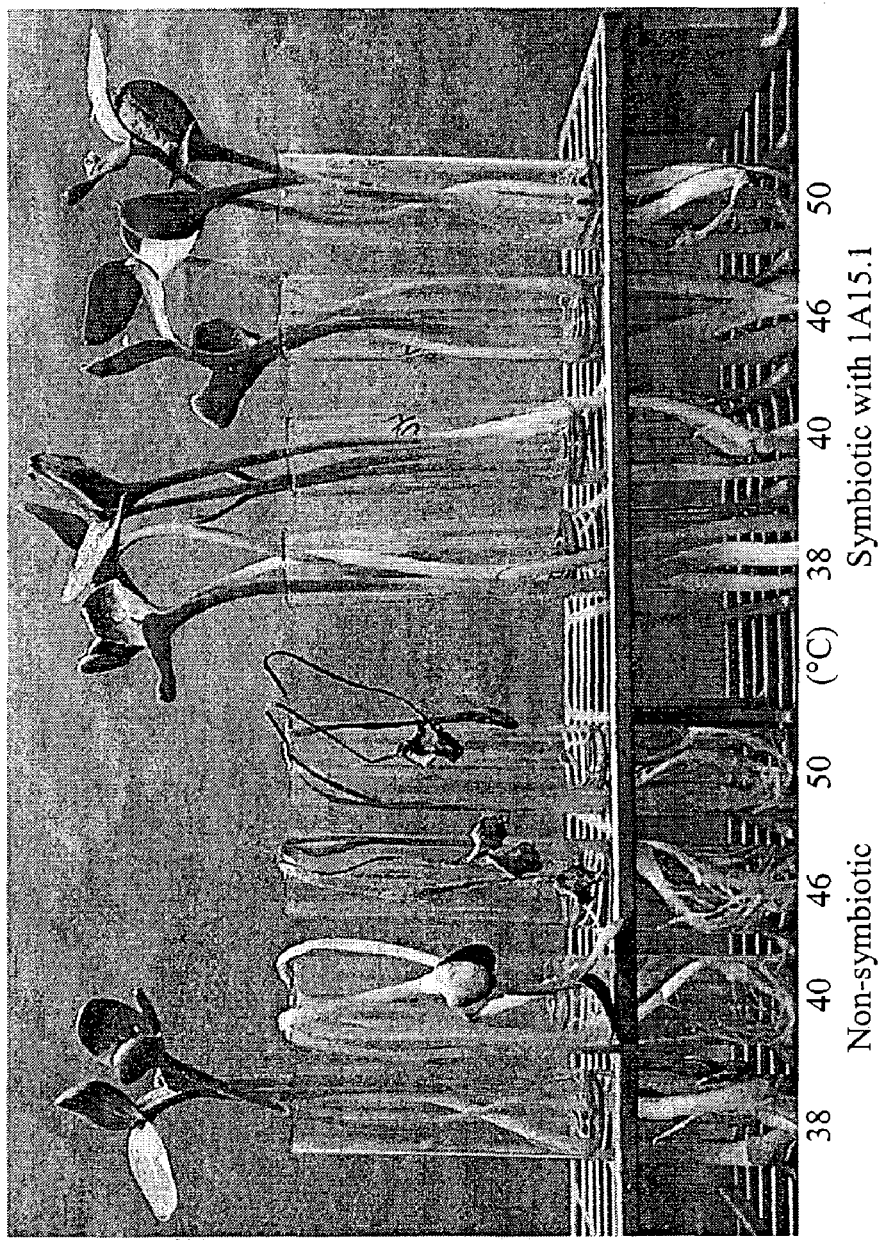

FIG. 3 depicts the thermotolerance of watermelon seedlings conferred by *Curvularia* sp. (isolate1A15.1). Seedlings were subjected to the indicated temperatures for 5 days and non-symbiotic seedlings began to wilt at 24 h (50° C.), 48 h (46° C.) and 72 h (40° C.).

Figure 4:
Figure 4:
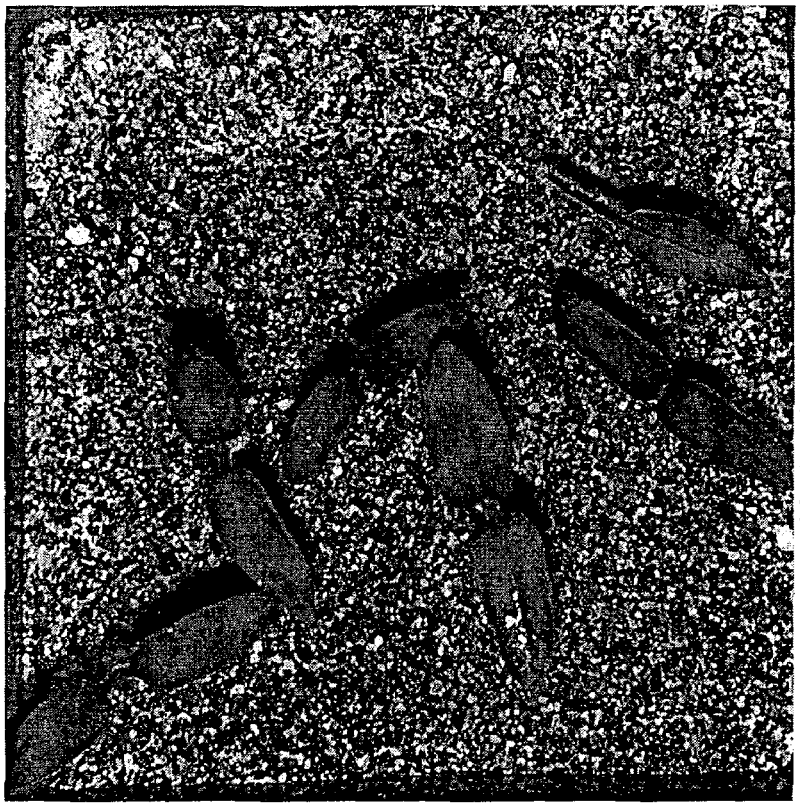

FIG. 4 depicts the thermotolerance of tomato seedlings conferred by *Curvularia* sp. (1A15.1). Seedlings were heat stressed at 50° C., and experiments were terminated at 7 days. Photos were taken at day 3.

Figure 5:
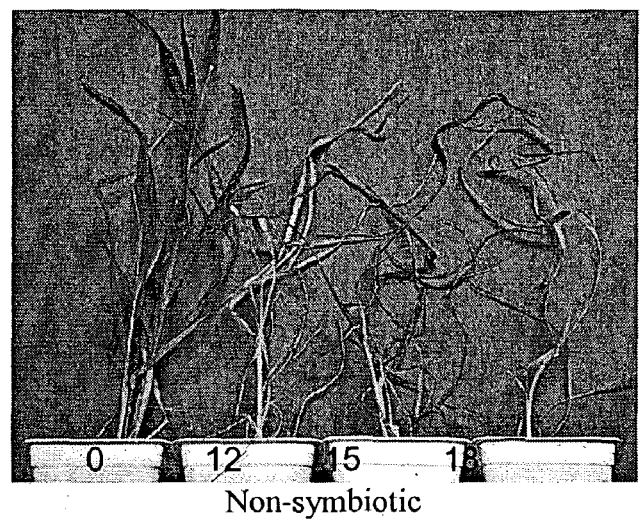
Figure 5:
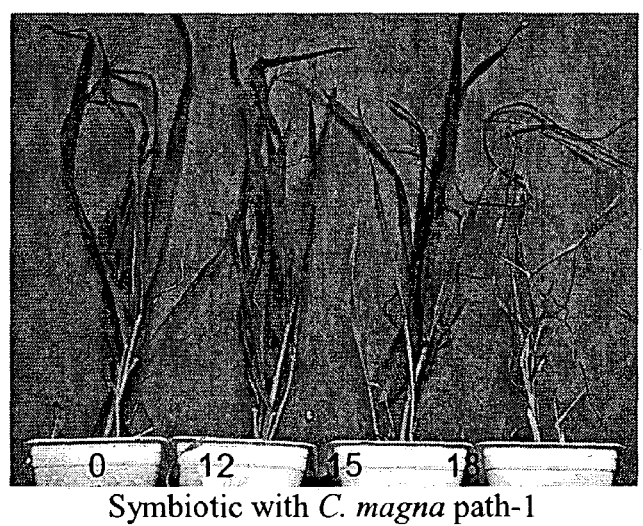
Figure 5:
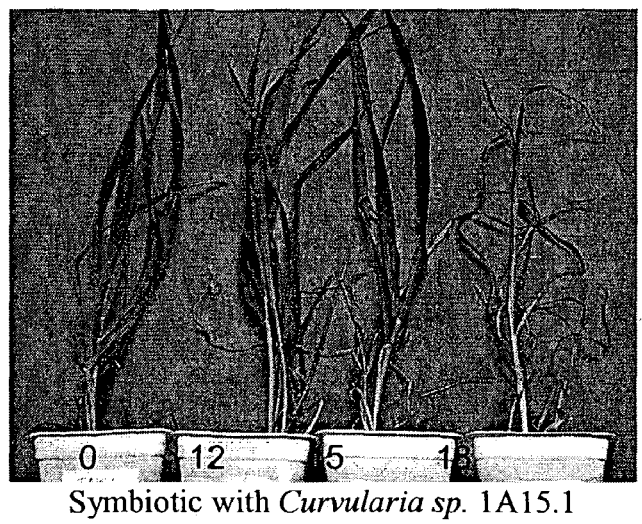

FIG. 5 depicts the drought tolerance of wheat conferred by *C. magna* (path-1) and *Curvularia* sp. (1A15.1). Watering was terminated successively throughout the experiment (days 0–18) to induce a gradient of drought. Water was added back after all but control plants had wilted. The numbers below each plant indicate the number of days the seedlings were without water.

DETAILED DESCRIPTION

The present invention is directed to methods and compositions of endophytic fungi that confer stress tolerance in inoculated plants, including both monocots and dicots. In particular, *Curvularia* species, isolated from a host grass *Dichanthelium languinosum* growing in the geothermal zones of Lassen Volcanic and Yellowstone National Parks, confers such stress tolerance. This endophytic fungi can be cultured in the absence of the host plant, and in the absence of the host plant, is not thermotolerant. That is, the survival of both the plant host and the endophyte in geothermal soils is dependent on a symbiotically conferred stress tolerance. However, upon inoculating a target plant or plant part, such as seedlings or seeds, the resulting plant shows stress tolerance, particularly drought and thermal tolerance. This shows that plant/fungal symbioses are able to adapt to habitat-specific selective pressures. This is the first such report of an endophyte conferring thermotolerance. Interestingly, the symbiotic communication responsible for thermal and drought tolerance is different since at least one host becomes drought, but not heat tolerant, when colonized by the fungus.

Accordingly, the present invention is directed to the use of certain endophytic fungi for the treatment of plants to confer stress tolerance. By "endophytic fungi" herein is meant a fungus that generally resides in the intracellular space of a plant. The endophytic fungi of the invention confer stress tolerance, in particular drought and/or thermal tolerance.

In a preferred embodiment, the endophytic fungi is a species of *Curvularia*. In a preferred embodiment, the *Curvularia* species is identified on the basis of morphological and genomic sequences, particularly rDNA sequences, as outlined herein. In general, these *Curvularia* species are isolated from host plants growing in geothermal soils, particularly those as discussed herein, such as acid rhyolite and siliceous sinter soils, at temperatures such as outlined in the Figures.

As will be appreciated by those in the art, there are a number of suitable *Curvularia* species that find use in the present invention. In particular, the species designated as isolate 1A15.1 is preferred, having the variable ITS1 and ITS2 regions and the constant region as outlined herein. *Curvularia* isolate 1A15.1, was deposited at the Agricultural Research Service Culture Collection (National Center for Agricultural Utilization Research, 1815 North University Street, Peoria, Ill.) on Mar. 28, 2006 and assigned accession no. NRRL 30910.

The endophytic fungi of the invention are useful in the treatment of target plants to confer stress tolerance. Suitable plants include both monocots and dicots (including eudicots) that can be colonized by the endophytic fungi of the invention. The plant may be at any stage of growth, including seeds, seedlings, or full plants. In addition, as discussed herein, any part of the plant may be inoculated; suitable plant parts include seeds, roots, leaves, flowers, stems, etc.

In a preferred embodiment, the target plant is a plant of the family Graminae (grasses). The grass plants into which these endophytes are introduced may be any of the useful grasses belonging to the genuses *Agropyron, Agrostis, Andropogon, Anthoxanthum, Arrhenatherum, Avena, Brachypodium, Bromus, Chloris, Cynodon, Dactylis, Elymus, Eragrostis, Festuca, Glyceria, Hierochloe, Hordeum, Lolium, Oryza, Panicum, Paspalum, Phalaris, Phleum, Poa, Setaria, Sorghum, Triticum, Zea* and *Zoysia*. In other words, this invention relates to grasses belonging to these genuses into which endophytes are artificially introduced. In the context of this invention, this also includes future generations of grasses.

In a preferred embodiment, the target plant is selected from the wheats, including, but not limited to, *Triticum monococcum, Triticum turgidum, Triticum timopheevi* (Timopheev's Wheat) and *Triticum aestivum* (Bread Wheat).

In a preferred embodiment, the target plant is a corn of the genus *Zea. Zea* is a genus of the family Gramineae (Poaceae), commonly known as the grass family. The genus consists of some four species: *Zea mays*, cultivated corn and teosinte; *Zea diploperennis* Iltis et al., diploperennial teosinte; *Zea luxurians* (Durieu et Asch.) Bird; and *Zea perennis* (Hitchc.) Reeves et Mangelsd., perennial teosinte.

Specific useful grasses include, but are not limited to, D languinsoum, rye grasses, and bluegrasses. Bluegrasses known in the art include Kentucky bluegrass, Canada bluegrass, rough meadow grass, bulbous meadow grass, alpine meadow grass, wavy meadow grass, wood meadow grass, Balforth meadow grass, swamp meadow grass, broad leaf meadow grass, narrow leaf meadow grass, smooth meadow grass, spreading meadow grass and flattened meadow grass.

In a preferred embodiment, the composition of the invention find use in the treatment of dicots, including eudicots such as tomato, watermelon, squash, cucumber, and *arabidopsis*.

This invention relates to target plants obtained by artificially introducing an endophyte into plants not containing filamentous endophytic fungi, i.e. plants not infected with an endophyte, and/or into infected plants from which endophytes have been removed. In the context of this invention, the endophyte which is artificially introduced into the target plant, e.g. the grasses, is an endophytic fungi that confers stress tolerance to the target plant.

These endophytes are discovered by looking for endophytes that live in plants growing in nature, subjecting them at least to a thermal or drought test, and artificially introducing those endophytes confirmed by the test to have such resistance.

The compositions of endophytic fungi of the invention are useful in conferring stress tolerance to plants and plant parts. "Stress" in this context is an environmental stress, including, but not limited to, high temperature (e.g. thermal stress), drought (e.g. lack of water), metals and metal ions, which cause a variety of plant problems and/or death, and abnormal pH (including both acidic and/or alkaline). The endophytic cultures outlined here allow the confirmation of stress resistance to the target plant.

In a preferred embodiment, the stress tolerance is thermal tolerance. In this case, while neither target plant nor fungi alone can survive in the elevated temperatures described herein, the culturing of the target plant with the fungi results in at least about a 5, 10, 20, 25 and 50% change in thermotolerance, as measured herein.

In a preferred embodiment, the stress tolerance is drought tolerance. In this case, while neither target plant nor fungi alone can survive in the decreased water conditions described herein, the culturing of the target plant with the fungi results in at least about a 5, 10, 20, 25 and 50% change in drought tolerance, as measured herein, and compared to controls lacking the fungus.

In a preferred embodiment, the stress tolerance is metal ion tolerance. As many of the soils from which these original host plants were isolated putatively contained metals, heavy metals and metal ions generally harmful to plants. However, the plants thrived upon inoculation with the endophytic fungus. Accordingly, the culturing of the target plant with the fungi results in at least about a 5, 10, 20, 25 and 50% change in metal tolerance, as measured herein, and compared to controls lacking the fungus.

In a preferred embodiment, the stress tolerance is pH tolerance. As many of the soils from which these original host plants were isolated had acidic pH levels which are generally harmful to plants. However, the plants thrived upon inoculation with the endophytic fungus. Accordingly, the culturing of the target plant with the fungi results in at least about a 5, 10, 20, 25 and 50% change in pH tolerance, as measured herein, and compared to controls lacking the fungus.

In a preferred embodiment, the endophytic compositions of the invention can confer growth enhancement. Growth enhancement is generally measured as a comparison of plants cultured with the endophytic fungi, e.g. *Curvularia*, with plants lacking the fungi. Differences in plant size, including leaf, root and stems are generally measured by weight, with increased growth being measured as at least about a 5–10% difference between controls and treated target plants, with at least about a 25% difference being preferred.

In a preferred embodiment, a pure culture of the endophytic fungi is used to inoculate plants or plant parts. A "pure culture" in this context means a culture devoid of other cultured endophytic fungi. The culture may be of spores, hyphae, mycelia, or other forms of the fungi, with spores being particularly preferred. In general, spores are used at $1-5\times10^{3-8}$ spores per plant with $1-3\times10^{4-6}$ being preferred and $1-3\times10^5$ being particularly preferred. As outlined herein, the endophytic fungi of the invention may be cultured in a variety of ways, including the use of PDA plates as shown in the invention, although liquid cultures may be done as well.

The spores or other innoculum may be placed on seed coats, particularly on seeds of endophytic fungi-free seeds (either naturally occurring or treated to remove any endophytes). It should be noted that the plants, including seeds, may be inoculated with combinations of endophytic fungal cultures, either different species each conferring stress tolerance, either the same type or different types. In addition, mixtures of *Curvularia* species may be used as well.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All references cited herein are incorporated by reference in their entirety.

EXAMPLES

Example 1

We report the first isolation of a fungal symbiont (*Curvularia* sp.) from a perennial grass (*D. lanuginosum*) inhabiting geothermal soils of Lassen Volcanic and Yellowstone National Parks. This plant-fungus symbiosis was mutualistic and provided thermotolerance to both host plant and fungal endophyte in laboratory experiments and field trials.

We collected approximately 200 *D. lanuginosum* plants from geothermal soils at more than ten different sites in two national parks. These soils are characterized as acid rhyolite and siliceous sinter, heated by geothermal activity (YNP Soil Scientists, Soil Investigation of the Reese Creek-McMinn Bench-Mammoth Area, Northwestern Yellowstone National Park, Wyo. National Park Service, Mammoth, Wyo. (1991) expressly incorporated by reference). Soil temperatures in Yellowstone Park were measured at depths of 5 and 15 cm with a datalogger (Campbell Scientific). Temperatures increased with soil depth and showed daily and annual fluctuations ranging from approximately 10–60° C. (FIG. 1).

Plants and their rhizospheres were removed with a trowel, individually placed in plastic ziplock bags, returned to the laboratory within 2 hours, and kept at 4° C. until further processing. Plants were washed and surface-sterilized by agitation in 70% ethanol for 5 min, 2% sodium hypochlorite for 20 min, 70% ethanol for 5 min, and then rinsed in sterile water. Fungal colonization was assessed by dissecting plants and plating sections on 0.1× Potato Dextrose Agar (PDA) medium (Redman, et al., Molec. Plant Microbe Inter. 12, 969–975 (1999) expressly incorporated by reference). The effectiveness of surface sterilization was verified by the imprint technique (Schulz, et al., Mycol. Res. 10, 1275–1283 (1999) expressly incorporated by reference).

*D. lanuginosum* plants of all ages, including young seedlings (2–4 leaf stage) were colonized by a fungal endophyte that was isolated from roots, crowns, leaves, and seed coats. Since seed coats were colonized by the fungus, seed coat transmission is likely the primary mode of colonization of young plants. Microscopic analysis also demonstrated that fungal hyphae were abundant in leaf and root tissues. Plants were fixed in Carnoy™s solution for 24 hr, cleared, and stained (Hignight, et al., Biotechn. Histochem. 68, 87–90 (1993) expressly incorporated by reference). A root cross section showed intercellular, melanized fungal hyphae in the outer cortex. Leaf analysis showed appressoria with penetrating germ tubes on the surface of the leaf with dark melanized hyphae growing into the leaf.

Single-spored cultures were isolated and the fungus was identified as a species of *Curvularia* by morphological (H. L. Barnett, B. B. Hunter, American Phytopathology Society, St. Paul, Minn. (1998) expressly incorporated by reference) and rDNA sequence (White, et al., in *PCR Protocols: A Guide to Methods and Applications*, M. A. Innis, D. H. Gelfand, J. J. Sninsky, T. J. White, Eds. (Academic Press, INC., San Diego, 1990) pp. 315–322) expressly incorporated by reference) analyses. Fungal DNA was prepared (Redman, et al., Molec. Plant Microbe Inter. 12, 969–975 (1999) expressly incorporated by reference) and the variable ITS1 and ITS2, and conserved 5.8S gene of the ribosomal RNA region was amplified by PCR with ITS 4 (5™-TCC TCC GCT TAT TGA TAT GC-3™) and ITS 5 (5™-GGA AGT AAA AGT CGT MC MGG-3™) primers as previously described (White, et al., in *PCR Protocols: A Guide to Methods and Applications*, M. A. Innis, D. H. Gelfand, J. J. Sninsky, T. J. White, Eds. (Academic Press, INC., San Diego, 1990) pp. 315–322). Fourteen single-spored isolates from various sites in Yellowstone and Lassen National Parks revealed 100% sequence similarity over 527 bp indicating that all of the plants were colonized by the same fungal species. Database comparisons of the 5.8S gene showed 100% similarity between the Yellowstone fungal endophyte and several species of *Curvularia* (GeneBank accession #'s AF071335-38, AF163077-84, AF212308, AF212310). The ITS 1 and 2 sequences collectively showed between 83 and 94% similarity to other *Curvularia* species (data not shown). However, only a 2% sequence difference occurs between some *Curvularia* species and few species have been sequenced (Berbee, et al., Mycologia 91, 964–977 (1999) expressly incorporated by reference), making species-level identification difficult. Therefore, we designated the fungal endophyte from *D. lanuginosum* as a *Curvularia* sp., termed isolate 1A15.1 herein. Interestingly, *Curvularia* species have not previously been identified as grass endophytes (Berbee, et al., Mycologia 91, 964–977 (1999)).

We examined the fungal community in soils surrounding *D. lanuginosum* plants For the presence of the endophyte as described (Redman, et al., Appl. Environ. Microbiol. 65, 5193–5197 (1999) expressly incorporated by reference). Soils collected from the base of 30 plants at three locations in Yellowstone Park had undetectable colony forming units (CFU) of the *Curvularia* sp., although several other fungal species were present in high numbers (Redman, et al., Appl. Environ. Microbiol. 65, 5193–5197 (1999) expressly incorporated by reference). Moreover, axenically-cultured *Cur-* vularia sp. was not capable of mycelial growth, spore germination, or survival at >40° C. on 0.1×PDA medium (Optimal mycelial growth and 100% spore germination of Curvularia sp. occurred at 25–35° C. Curvularia sp. spores failed to germinate at >40° C., and only 14% germinated at 37° C. on 0.1×PDA medium; mycelial plugs grew at 35° C., but failed to grow at 40° C.; mycelium or spores incubated for three days at 50° C. and then transferred back to 25 or 35° C. failed to resume growth, or germinate, respectively on 0.1× PDA medium. Spores inoculated into sterile sand and incubated for three days at 50° C., or at 70° C. intermittently (10 hours followed by 37° C. for 14 hours) for ten days also failed to germinate when plated on 0.1× PDA medium at 25° C. All growth and germination assays were independently repeated at least three times.). Since thermal soils were above 40° C. all summer (FIG. 1) and the fungus was undetected in geothermal soils surrounding plants, we conclude that the endophytic Curvularia sp. was exclusively associated with plants in geothermal soils.

To assess the effect of the endophyte on the thermotolerance of D. lanuginosum we generated endophyte-free plants. D. lanuginosum seeds were scarified to remove the seed coat and surface-sterilized (Stout, et al., Plant Science 130, 1–9 (1997) expressly incorporated by reference). Seeds were germinated on 1% (w/v) agar plates and demonstrated to be endophyte-free by surface-sterilization and the imprint technique as described above. Seedlings at the 3-leaf stage were transferred individually to sterile magenta boxes (FIG. 2A). To generate symbiotic plants, 1–3×10 5 spores were pipetted onto plants between the crown and first leaf. Fungal colonization of plants was verified by dissecting and plating surface-sterilized plant sections as described above. Magenta boxes were placed in a thermal soil simulator where thermal tape was wrapped around the boxes to heat the sand in the magenta boxes (FIG. 2B).

Endophyte-free D. lanuginosum (45/45 plants) became shriveled and chlorotic at 50° C. (data not shown). In contrast, symbiotic plants (45/45) tolerated constant 50° C. soil temperature for three days, and intermittent soil temperatures as high as 70° C. (for 10 hours followed by 37° C. for 14 hours, FIG. 4C) for ten days. All non-symbiotic plants (45/45) died after the 70° C. heat regime (FIG. 4D), whereas symbiotic plants (45/45) survived. The endophyte was re-isolated from surface sterilized roots and leaves of all surviving plants indicating that both the fungus and the host were protected from thermal stress. We also placed colonized and uncolonized seedlings in pasteurized geothermal soil collected and returned to Amphitheater Springs in Yellowstone in May, 2001 After the summer season, most of the plants went senescent for the winter season and colonized plants were not visibly healthier than uncolonized plants (not shown). By the spring of 2002, however, colonized plants were distinctly more robust and green than non-symbiotic plants, especially at higher soil temperatures (Table 1). Indeed, at the highest temperature (45° C.), non-symbiotic plants did not survive. Symbiotic plants had significantly more new shoots, and greater root and total mass (Table 1). Moreover, the beneficial effect of fungal symbiosis increased with soil temperatures, demonstrating that Curvularia sp. provided thermal protection for D. lanuginosum.

Although we did not observe visible differences between symbiotic and non-symbiotic plants until the spring of 2002, it is likely that thermal protection occurred throughout the year since the benefits of symbiosis were not always obvious until we assessed plant biomasses which required plant removal.

TABLE 1

| Soil Temp. | Plant Status | New Shoots | Plant Biomass (g) | | | P-value |
|---|---|---|---|---|---|---|
| | | | Roots | Leaves | Total | |
| 30° C. | NS-a | 43 | 3.8 | 11 | 14.8 | 0.05 |
| | NS-b | 21 | 4.2 | 13.4 | 17.6 | |
| | S-a | 63 | 6.6 | 16.8 | 23.4 | |
| | S-b | 57 | 7.3 | 14.8 | 22.1 | |
| 35° C. | NS-a | 39 | 3.8 | 17.3 | 21.1 | 0.083 |
| | NS-b | 46 | 3.3 | 18.9 | 22.2 | |
| | S-a | 63 | 4.3 | 26.1 | 30.4 | |
| | S-b | 57 | 5 | 21.4 | 26.4 | |
| 40° C. | NS-a | 10 | 2 | 4 | 6 | 0.045 |
| | NS-b | 10 | 4.4 | 7.2 | 11.6 | |
| | S-a | 38 | 5.9 | 17.2 | 23.1 | |
| | S-b | 36 | 6.8 | 14.5 | 21.3 | |
| 45° C. | NS-a | 0 | 0 | 0 | 0 | 0.012 |
| | NS-b | 0 | 0 | 0 | 0 | |
| | S-a | 24 | 3.2 | 10.2 | 13.4 | |
| | S-b | 23 | 5.4 | 11.4 | 16.8 | |

We re-isolated Curvularia sp. from D. lanuginosum roots at 45° C. field soil temperatures, confirming our laboratory experiments that demonstrated thermal protection for the fungus as well as its plant host. This is the first demonstration of thermotolerance provided to both symbiotic partners as a result of their mutualistic interaction. The endophytic Curvularia sp. was exclusively associated with plants in geothermal soils and 100% of the plants were colonized with this endophyte. Therefore, we conclude that this mutualism is responsible for the adaptation of these two organisms to the geothermal soil environment.

Example 2

We tested the host range and symbiotic lifestyle expression of D. lanuginosum endophyte, Curvularia sp., isolate 1A15.1, in phylogenetically distant monocots and eudicots not previously known to be hosts. One week old monocot (wheat, corn) and eudicot (squash, cucumber, watermelon, tomato, arabidopsis) seedlings were either mock-inoculated or inoculated with 1A15.1 (Redman, et al., Thermotolerance conferred to plant host and fungal endophyte during mutualistic symbiosis, Science In Press (2003) expressly incorporated by reference). Colonization control plants were inoculated with a uv-induced mutant (path-1)(Freeman, S. & Rodriguez, R. J., Genetic conversion of a fungal plant pathogen to a nonpathogenic, endophytic mutualist. Science 260, 75–78 (1993) expressly incorporated by reference) of Colletotrichum magna that asymptomatically colonizes these hosts (except corn) and expresses a mutualistic, rather than a pathogenic, lifestyle (Redman, et al., New Phytol. 151, 705–716 (2001)). After two weeks of growth, plants were surface-sterilized and assessed for fungal colonization (Redman, et al., New Phytol. 151, 705–716 (2001)). With the exception of corn seedlings, all plants were asymptomatically colonized by path-1 and 1A15.1 in root and stem tissue (Table 2). Both 1A15.1 and path-1 had host ranges that encompassed monocots and eudicots.

TABLE 2

| Plants | | | path-1 | | | | 1A15.1 | | | |
| --- | --- | --- | --- | --- | --- | --- | --- | --- | --- | --- |
| | | | Colonization | | Stress Tolerance | | Colonization | | Stress Tolerance | |
| Family | Genus | Species | Roots | Stem | Drought | Thermal | Roots | Stem | Drought | Thermal |

| | Family | Genus | Species | Roots | Stem | Drought | Thermal | Roots | Stem | Drought | Thermal |
| --- | --- | --- | --- | --- | --- | --- | --- | --- | --- | --- | --- |
| Eudicots | | | | | | | | | | | |
| Squash | Cucurbitaceae | Cucurbita | pepo | + | + | nt | nt | + | + | nt | nt |
| Cucumber | Cucurbitaceae | Cucumis | sativus | + | + | nt | nt | + | + | nt | nt |
| Watermelon | Cucurbitaceae | Citrullus | lanatus | + | + | + | − | + | + | + | + |
| Tomato | Solanaceae | Lycopersicon | esculentum | + | + | + | − | + | + | + | + |
| Arabidopsis | Brassicaceae | Arabidopsis | thaliana | + | + | − | − | + | + | + | + |
| Monocots | | | | | | | | | | | |
| Panic grass* | Poaceae | Dichanthelium | lanuginosum | + | + | nt | − | + | + | + | + |
| Wheat | Poaceae | Triticum | aestivum | + | + | + | − | + | + | + | − |
| Corn | Poaceae | Zea | mays | − | − | nt | nt | − | − | nt | nt | nt = not tested,
*= data from Redman et al., 2003.

To determine the type of symbiosis established between 1A15.1 and nonthermal-adapted plants, endophyte-colonized (symbiotic) and mock-inoculated (non-symbiotic) wheat, arabidopsis, watermelon and tomato plants were generated and exposed to temperature stress (Redman, et al., Science In Press (2003)). Curvularia sp. conferred temperature tolerance to watermelon exposed to 50, 46, and 40° C. for 24, 48, and 72 h, respectively, whereas non-symbiotic plants wilted and died during these treatments (FIG. 3). Symbiotic plants showed no wilting 5 days after exposure to these temperatures. From surviving roots and stems of all symbiotic plants treated at 50° C., the fungus was re-isolated (Redman, et al., New Phytol. 151, 705–716 (2001)), indicating that it was also protected from heat stress, as previously observed with this endophyte in its host D. lanuginosum (Redman, et al., Science In Press (2003)). In contrast, C. magna path-1 colonized, but did not confer temperature tolerance to these hosts (not shown). This was unsurprising since path-1 was obtained by mutation of wild-type C. magna, which is pathogenic on cucurbits, and was used as a nonthermal-adapted endophyte control.

Curvularia sp. also conferred heat tolerance to tomato (FIG. 4) and arabidopsis seedlings (not shown) exposed to 50° C. for 7 days. Non-symbiotic plant leaves curled and died after 3–5 days of thermal stress, whereas symbiotic plant leaves did not. All surviving symbiotic plants were surface-sterilized and assayed for fungal colonization (Redman, et al., New Phytol. 151, 705–716 (2001)), and, again, all were colonized by Curvularia sp. We conclude that the adaptive symbiotic communication resulting in thermotolerance of a monocot host (D. lanuginosum) is the same in at least some eudicot hosts. This suggests that the genetic and biochemical bases of this adaptive symbiotic communication is conserved and evolved prior to the divergence of monocots and eudicots that occurred between 175–230 million years ago (Zhou, J. & Kleinhofs, A., Molecular evolution of nitrate reductase genes. J. of Mol. Evol. 42, 432–442 (1996); Yang, et al., Rates of nucleotide substitution in angiosperm mitochondrial DNA sequences and dates of divergence between Brassica and other angiosperm lineages. J. Mol. Evol. 48, 597–604 (1999) all of which are expressly incorporated by reference). This is the first report of adaptive symbiotic benefits conferred by an endophytic fungus being transferred from monocots to eudicots.

Although thermotolerance was not conferred to wheat, Curvularia sp. did confer drought tolerance (FIG. 5). Wheat plants colonized by either Curvularia sp. or C. magna path-1 survived more days (up to 18 days) of water deprivation than non-symbiotic plants (less than 12 days). This supports previous observations that the outcome of symbiosis and the specific mutualistic benefits conferred to hosts is dependent on the plant genotype (Smith, K. P. & Goodman, R. M., Annu. Rev. Phytopathol. 37, 473–492 (1999); Redman, et al., New Phytol. 151, 705–716 (2001); Marks, S. & Clay, K., Physiological responses of Festuca arundinacea to fungal endophyte, New Phytol. 133, 727–733 (1996) all of which are expressly incorporated by reference). This finding also demonstrated that the symbiotic communication resulting in drought and heat tolerance were different, since drought tolerance was conferred without concomitant heat tolerance to wheat.

Symbiotically conferred abiotic and biotic stress tolerance appears to involve two mechanisms: 1) rapid activation of host stress response systems after symbiotic plants are exposed to stress (Redman, R. S. et al., Plant Physiol. 119, 795–804 (1999) expressly incorporated by reference), or 2) synthesis of anti-stress biochemicals by the fungus (Bacon, C. W. & Hill, N. S., Symptomless grass endophytes: products of coevolutionary symbioses and their role in the ecological adaptations of grasses, in Endophytic fungi in grasses and woody plants (eds. Redkin, S. C. & Carris, L. M.) 155–178 (APS Press, St. Paul, 1996) expressly incorporated by reference). The only known anti-stress biochemicals produced by endophytic fungi are alkaloids which decrease plant herbivory (Siegel, M. R. & Bush, L. P. Toxin production in grass/endophyte associations, in The Mycota (eds. Carroll, G. C. & Tudzynski, P.) 185–207 (Springer-Verlag, Heidelberg, 1997) expressly incorporated by reference). Many of the endophytes that produce anti-herbivory alkaloids also confer drought tolerance to host plants (Bacon, C. W. & Hill, N. S., in Endophytic fungi in grasses and woody plants (eds. Redkin, S. C. & Carris, L. M.) 155–178 (APS Press, St. Paul, 1996) expressly incorporated by reference). Although the mechanism of conferred drought tolerance is unknown, it correlates with the activation of host stress response systems (Auge, R. M. Stomatal, Behavior of arbuscular mycorrhizal plants, in Arbuscular Mycorrhizas: Physiology and Function (eds. Kapulnik, Y. & Douds, D. D.) 201–236 (Kluwer Academic Publishers, Dordrecht, 2000)

expressly incorporated by reference). It is not known how endophytes activate host abiotic stress response systems or if there are additional mechanisms involved in symbiotically conferred stress tolerance. Regardless, mutualistic fungi can provide fitness benefits that contribute to the adaptation and survival of host plants.

Methods

Host Inoculation

Seeds were surface-sterilized and planted in vermiculite (watermelon) or sand (all other hosts listed in Table 2) until seedlings were established (Redman, et al., Thermotolerance conferred to plant host and fungal endophyte during mutualistic symbiosis, Science In Press (2003)). Seedlings were either mock-inoculated or inoculated with 1A15.1 by pipetting $10^5$ spores at stem bases and incubated for 72 h in a growth chamber (Redman, et al., New Phytol. 151, 705–716 (2001)).

Thermotolerance Assay

Watermelon seedlings were transferred to glass tubes containing water that covered the roots and lower stems, and the tubes were inserted to the water surface level in sand heated to 38, 40, 46 or 50° C. Temperature was monitored daily and water levels were maintained throughout the experiment which was terminated after 5 days. Watermelon assays were repeated five times with a total of 30 symbiotic and 30 non-symbiotic plants tested at each temperature. A thermal soil simulator was used to heat only the root zones of other host plants listed in Table 2 (Redman, et al., Thermotolerance conferred to plant host and fungal endophyte during mutualistic symbiosis, Science In Press (2003)). Root zones were heated at 50° C. for 7 days. Experiments with each host were repeated three times for a total of 20 symbiotic and 20 non-symbiotic plants. All plants surviving thermal treatment were tested for fungal colonization.

Drought Tolerance Assay

Watering of inoculated and mock-inoculated, established seedlings was terminated on different days (0–18 days) to induce a gradient of drought stress. Plants were left unwatered until all except the control plants wilted. Water was then added back and plants were photographed after a 48 h recovery. Drought tolerance assays were repeated three times with a total of 20 symbiotic and 20 non-symbiotic plants of each host.

Host Colonization Assay

Surviving plants were surface-sterilized, cut into sections and section placed on 0.1× Potato Dextrose Agar medium to assess fungal colonization (Redman, et al., New Phytol. 151, 705–716 (2001)).

ADDITIONAL REFERENCES

1. O. Petrini, in *Microbiology of the Phyllosphere* N. J. Fokkema, J. van den Heuvel, Eds. (Cambridge University Press, Cambridge, 1986) pp. 175–187.
2. K. Saikkonen, S. H. Faeth, M. Helander, T. J. Sullivan, *Annu. Rev. Ecol. Syst.* 29, 319–343 (1998).
3. J. K. Stone, C. W. Bacon, J. F. White Jr., in *Microbial Endophytes* C. W. Bacon, J. F. White Jr., Eds. (Marcel Dekker, Inc., New York, 2000) pp. 3–29.
4. A. Varma, et al., *Appl. Environ. Microbiol.* 65, 2741–2744 (1999).
5. G. A. Kuldau, I. E. Yates, in *Microbial Endophytes* C. W. Bacon, J. F. White Jr., Eds. (Marcel Dekker, Inc., New York, 2000) pp. 85–117.

We claim:

1. A method of treating a target plant to confer stress tolerance comprising inoculating said plant or a part of said plant with a culture of *Curvularia* isolate 1A15.1, deposit number NRRL 30910, wherein said stress tolerance is chosen from the group consisting of thermal tolerance and drought tolerance.

2. A method of treating a plant according to claim 1 wherein said plant is a monocot or said plant part is from a monocot.

3. A method of treating a plant according to claim 2 wherein said monocot is a grass.

4. A method of treating a plant according to claim 2 wherein said monocot is a wheat.

5. A method of treating a plant according to claim 1 wherein said plant is a dicot or said plant part is from a dicot.

6. A method of treating a plant according to claim 5 wherein said dicot is a eudicot.

7. A method of treating a plant according to claim 1 wherein said plant part is a seed.

8. A method of treating a plant according to claim 1 wherein said plant part is a seedling.

* * * * *

UNITED STATES PATENT AND TRADEMARK OFFICE
CERTIFICATE OF CORRECTION

| | | |
|---|---|---|
| PATENT NO. | : 7,232,565 B2 | Page 1 of 1 |
| APPLICATION NO. | : 10/602546 | |
| DATED | : June 19, 2007 | |
| INVENTOR(S) | : Joan M. Henson et al. | |

It is certified that error appears in the above-identified patent and that said Letters Patent is hereby corrected as shown below:

On the Title Page, item [73], Assignee should read "Montana State University"

and "Government of the United States of America, Represented by the

Secretary of the Department of the Interior"

Signed and Sealed this

Twenty-second Day of July, 2008

JON W. DUDAS
*Director of the United States Patent and Trademark Office*